US012752016B2

(12) United States Patent
Klein

(10) Patent No.: US 12,752,016 B2
(45) **Date of Patent: *Oct. 6, 2026**

(54) DRUG CONTAINING TARGETING LIPOSOMES

(71) Applicant: NEXTAGE THERAPEUTICS LTD., Nes Ziona (IL)

(72) Inventor: Joseph Yeshayahu Klein, Haifa (IL)

(73) Assignee: NEXTAGE THERAPEUTICS LTD., Nes Ziona (IL)

( * ) Notice: Subject to any disclaimer, the term of this patent is extended or adjusted under 35 U.S.C. 154(b) by 1227 days.

This patent is subject to a terminal disclaimer.

(21) Appl. No.: 17/638,988

(22) PCT Filed: Aug. 31, 2020

(86) PCT No.: PCT/IL2020/050946

§ 371 (c)(1),
(2) Date: Feb. 28, 2022

(87) PCT Pub. No.: WO2021/038573

PCT Pub. Date: Mar. 4, 2021

(65) Prior Publication Data

US 2022/0305137 A1 Sep. 29, 2022

Related U.S. Application Data

(60) Provisional application No. 62/894,794, filed on Sep. 1, 2019.

(51) Int. Cl.

| | |
|---|---|
| ***A61K 47/00*** | (2006.01) |
| ***A61K 47/62*** | (2017.01) |
| ***A61K 47/69*** | (2017.01) |
| ***A61P 25/00*** | (2006.01) |

(52) U.S. Cl.

CPC .......... *A61K 47/6911* (2017.08); *A61K 47/62* (2017.08); *A61P 25/00* (2018.01)

(58) Field of Classification Search

CPC .... A61K 47/6911; A61K 47/62; A61K 9/127; A61K 31/517; A61K 31/704; A61P 25/00; C07K 7/06

See application file for complete search history.

(56) References Cited

U.S. PATENT DOCUMENTS 9,655,848 B2 5/2017 Allon

FOREIGN PATENT DOCUMENTS

| | | |
|---|---|---|
| JP | H04208296 | 7/1992 |
| JP | H04295497 | 10/1992 |
| WO | 0103668 | 1/2001 |
| WO | 2014076709 | 5/2014 |
| WO | 2018/193458 | 10/2018 |

OTHER PUBLICATIONS

Kim et al. Methionine oxidation and reduction in proteins' Biochimica et Biophysica Acta (1840) 2014 pp. 901-905.*

Ying M, et al. Liposome-based systemic glioma-targeted drug delivery enabled by all-D peptides. ACS Applied Materials and Interfaces. 2016; 8(44):29977-85. Published Oct. 31, 2016 (Oct. 31, 2016).

Zhang W, et al. Targeting prostate cancer cells with hybrid elastin-like polypeptide/liposome nanoparticles. International Journal of Nanomedicine. 2018; 13:293. Published online Jan. 9, 2018 (Jan. 9, 2018).

Chang HI, Yeh MK. Clinical Development of liposome-based drugs: formulation, characterization, and therapeutic efficacy. International Journal of Nanomedicine. 2012; 7(49). Published online Dec. 30, 2011 (2011-12-30).

Fanny Astruc-Diaz: "Cannabinoids delivery systems based on supramolecular inclusion complexes and polymeric nanocapsules for treatment of neuropathic pain", Human Health and Pathology, Universite Claude Bernard—Lyon 1, Jan. 23, 2014 (Jan. 23, 2014), pp. 1-277.

Mackay J. Andrew et al: HIV TAT Peptide Modifies the Distribution of DNA Nanolipoparticles Following Convenction-enhanced Delivery, Molecular Therapy, vol. 16, No. 5, May 1, 2008 (May 1, 2008), pp. 893-900.

Aparicio-Blanco Juan et al: "Lipid nanocapsules decorated and loaded with cannabidiol as targeted prolonged release carriers for glioma therapy: In vitro screening of critical parameters", European Journal of Pharmaceutics and Biopharmaceutics, vol. 134, Nov. 22, 2018 (Nov. 22, 2018), pp. 126-137.

* cited by examiner

*Primary Examiner* — Jeanette M Lieb

(74) *Attorney, Agent, or Firm* — JMB Davis Ben-David

(57) ABSTRACT

Described herein are novel, modified targeting peptides which can be incorporated within liposomes. Additionally, described herein are liposomes containing the modified targeting peptides. Liposomes preferably comprise a lipid-based bilayer and at least one drug. Also provided herein are methods for making the modified targeting peptides, and the liposomes, and methods for treatment of diseases of the CNS using the liposomes.

17 Claims, 7 Drawing Sheets

Specification includes a Sequence Listing.

n=3

SEQUENCE LISTING

```
<160> NUMBER OF SEQ ID NOS: 1

<210> SEQ ID NO 1
<211> LENGTH: 7
<212> TYPE: PRT
<213> ORGANISM: Artificial Sequence
<220> FEATURE:
<223> OTHER INFORMATION: Synthetic polypeptide
<220> FEATURE:
<221> NAME/KEY: MISC_FEATURE
<222> LOCATION: (6)..(6)
<223> OTHER INFORMATION: Optionally M is oxidized or methionine
      sulfoxide

<400> SEQUENCE: 1

Ala His Arg Glu Arg Met Ser
1               5
```

DRUG CONTAINING TARGETING LIPOSOMES

CROSS REFERENCE TO RELATED APPLICATIONS

This is the U.S. National Stage of International Patent Application No. PCT/IL2020/050946, filed Aug. 31, 2020, which claims priority to U.S. Provisional Patent Application 62/894,794, filed Sep. 1, 2019; the contents of which is incorporated by reference herein in its entirety.

FIELD

Provided herein are liposomes containing a drug, and a targeting agent.

BACKGROUND

Blood vessels deliver nutrients and oxygen to cells of the body. The blood vessels which bring nutrients and oxygen to the central nervous system (CNS), and particularly to the brain, are unique in that various blood components are restricted from passing from capillaries into the brain. This border, which is formed by tight junctions between endothelial cells, forms the blood-brain barrier in mammals. The blood-brain barrier protects the brain from pathogens and inhibits passage of various solutes and hydrophilic molecules, while allowing passage of oxygen, carbon dioxide and various small molecules into the brain. Some solutes necessary for brain function are actively transported across the blood-brain barrier.

While some pharmaceutical agents may be administered systemically to circulate in the vasculature of a mammal and reach a target tissue or organ, these pharmaceutical agents may be blocked from reaching the brain due to the blood-brain barrier. This makes delivery of pharmaceuticals to the brain, particularly for the treatment of neurological disorders and/or CNS neoplasms difficult.

SUMMARY

Described herein are novel, modified targeting peptides which can be incorporated within liposomes.

Additionally, described herein are liposomes containing the modified targeting peptides. Liposomes preferably comprise a lipid-based bilayer and at least one drug.

Also provided herein are methods for making the modified targeting peptides, and the liposomes, and methods for treatment of diseases of the CNS using the liposomes.

The foregoing and other objects, features, and advantages will become more apparent from the following detailed description, which proceeds with reference to the accompanying figures.

BRIEF DESCRIPTION OF DESCRIBED SEQUENCES

Figure 1:
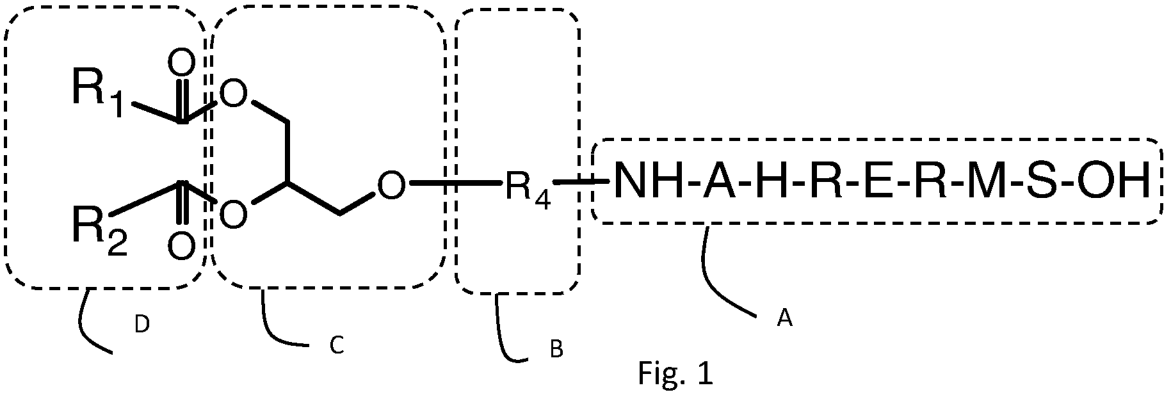
FIG. 1 is a structural formula of a modified targeting peptide according to an embodiment, showing moieties which it contains.
Figure 2A:
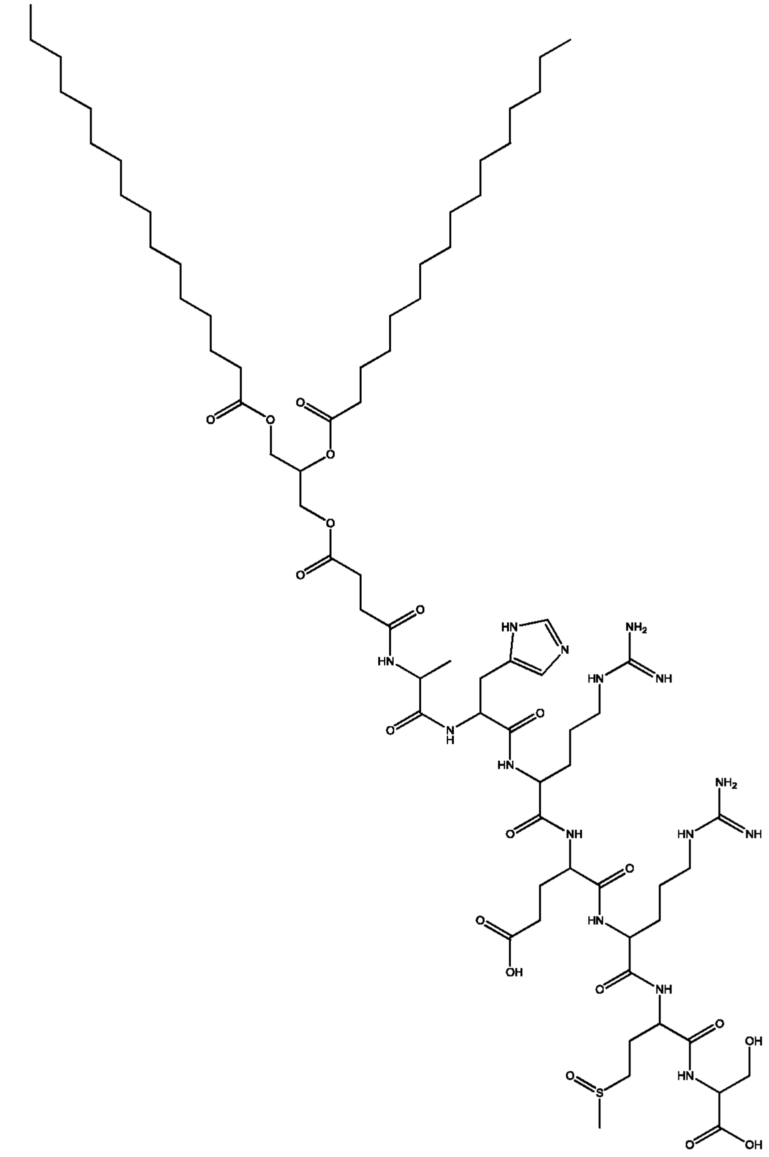
FIGS. 2A-2E are structural formulae of a modified targeting peptides (compounds 8, 12, 16, 20 and 24) according to an embodiment wherein methionine is in its oxidized form, in the form of methionine sulfoxide, having either ester-amide or ether amide linkers, wherein the n number indicates the number methylene groups between the ester/ether and the amide group.
Figure 2B:
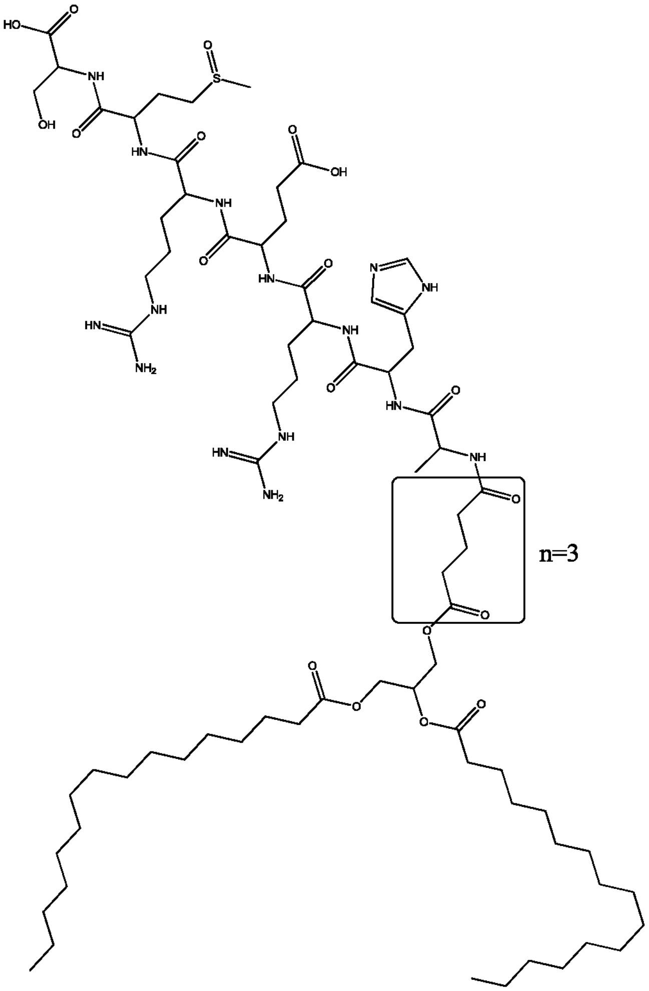
Figure 2C:
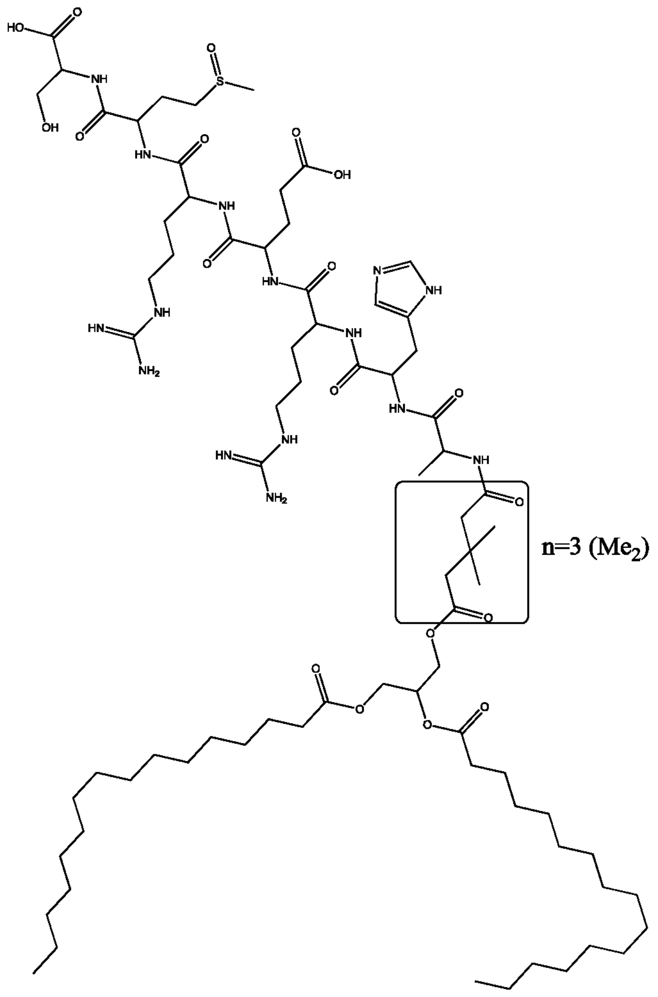
Figure 2D:
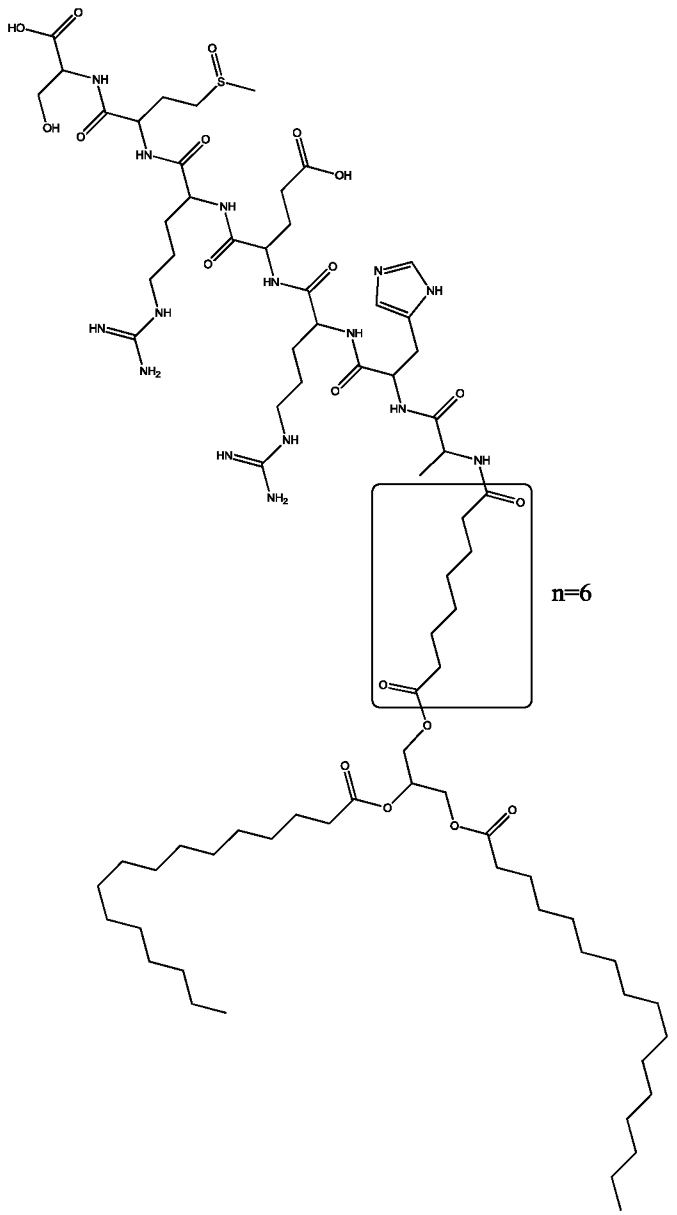
Figure 2E:
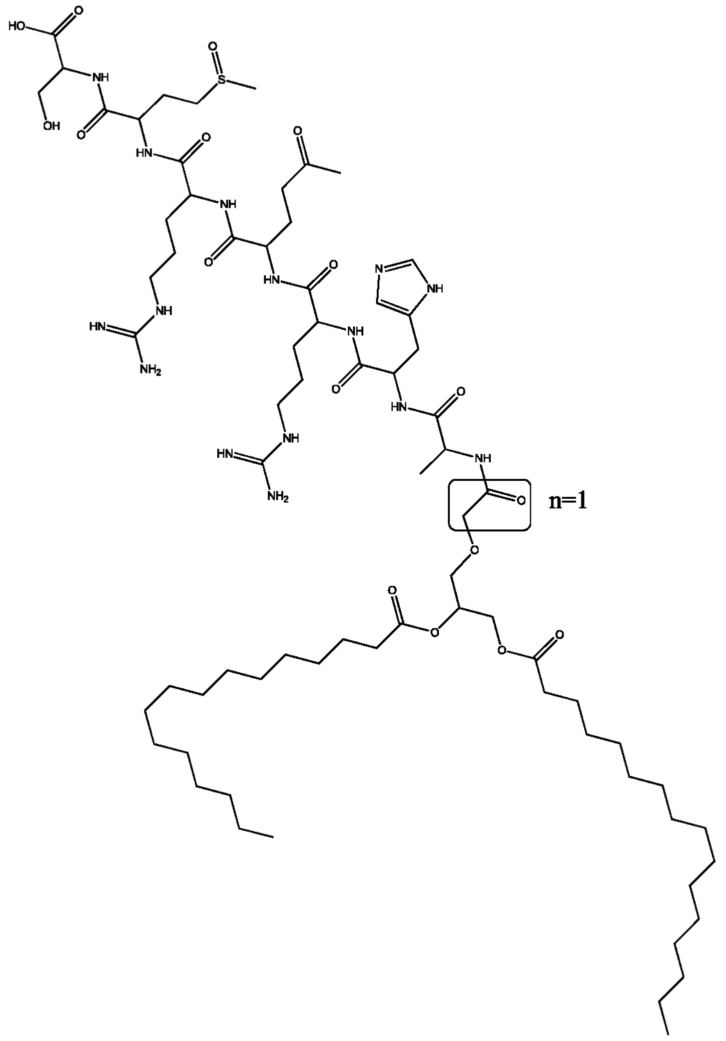

The nucleic and amino acid sequences provided herewith are shown using standard letter abbreviations for nucleotide bases, and three letter code for amino acids, as defined in 37 C.F.R. 1.822. Only one strand of each nucleic acid sequence is shown, but the complementary strand is understood as included by any reference to the displayed strand.

SEQ ID NO: 1 is the amino acid sequence of a targeting peptide, having the sequence: AHRERMS. Optionally, the methionine residue is oxidized.

DETAILED DESCRIPTION

I. Terms

Unless otherwise noted, technical terms are used according to conventional usage. Definitions of common terms in molecular biology can be found in Benjamin Lewin, *Genes V*, published by Oxford University Press, 1994 (ISBN 0-19-854287-9); Kendrew et al. (eds.), *The Encyclopedia of Molecular Biology*, published by Blackwell Science Ltd., 1994 (ISBN 0-632-02182-9); and Robert A. Meyers (ed.), *Molecular Biology and Biotechnology: a Comprehensive Desk Reference*, published by VCH Publishers, Inc., 1995 (ISBN 1-56081-569-8).

Unless otherwise explained, all technical and scientific terms used herein have the same meaning as commonly understood by one of ordinary skill in the art to which this disclosure belongs. The singular terms "a," "an," and "the" include plural referents unless context clearly indicates otherwise. Similarly, the word "or" is intended to include "and" unless the context clearly indicates otherwise. It is further to be understood that all base sizes or amino acid sizes, and all molecular weight or molecular mass values, given for nucleic acids or polypeptides are approximate, and are provided for description. Although methods and materials similar or equivalent to those described herein can be used in the practice or testing of this disclosure, suitable methods and materials are described below. The term "comprises" means "includes." The abbreviation, "e.g." is derived from the Latin exempli gratia, and is used herein to indicate a non-limiting example. Thus, the abbreviation "e.g." is synonymous with the term "for example."

In case of conflict, the present specification, including explanations of terms, will control. In addition, all the materials, methods, and examples are illustrative and not intended to be limiting.

Biological Marker: a measurable, quantifiable indicator which is indicative of a presence of a disease or a medical condition. A biological marker, for example, may be body temperature, an antibody, glucose, or a protein.

Blood-brain barrier recognition peptide: a peptide which facilitates the penetration of the liposomal carrier to which the recognition peptide is attached, to the brain from a circulatory system (blood) by binding to a specific transporter located within the blood-brain barrier.

Liposome: a composite, generally spherical vesicle comprising a lipid layer or lipid bilayer, or multi-layer. Liposomes are typically formed from phospholipids and may be used to encapsulate active pharmaceutical agents or entrap the pharmaceutical agents within the lipid layer.

Radiotherapeutic agent: an agent, usually in the form of a radioactive element, which emits radiation, such as alpha radiation, gamma radiation or beta radiation.

II. Overview of Several Embodiments

Modified Targeting Peptides:

Provided herein are modified targeting peptides which can be used to prepare modified targeting peptides and liposomes. According to an embodiment, a modified targeting peptide has a general structure according to Formula [I]:

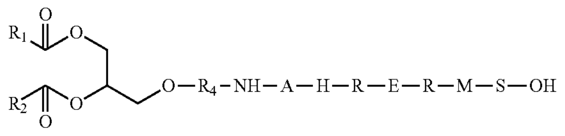

wherein $R_1$ and $R_2$ are the same or different and are an alkyl chain having between 13 and 19 carbon atoms, and wherein $R_4$ is a linker having the structure $R_6—R_5—R_7$, wherein $R_6$ and $R_7$ are each independently a bond or a carbonyl group; and $R_5$ is selected from the group consisting of: $C_{1-20}$ straight alkyl, $C_{3-20}$ branched alkyl, $C_{3-20}$ cyclic alkyl, and $C_{6-20}$ arylalkyl. Preferably, $R_1$ and $R_2$ are a linear (non-branched) alkyl chain having 15 carbon atoms. Preferably, the modified targeting peptide has the structure:

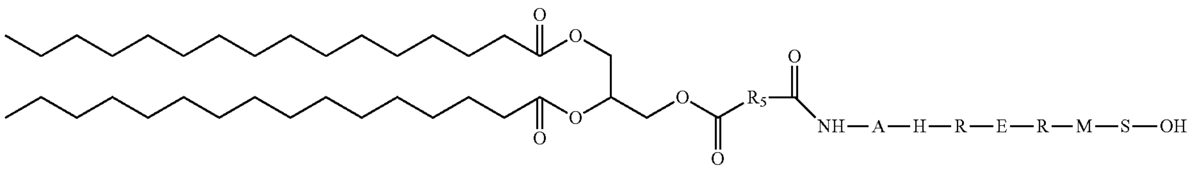

A modified targeting peptide according to an embodiment comprises a structure according to Formula [I] as depicted in FIG. 1. Modified targeting peptide comprises a peptide portion A, a linker portion B, a glycerol moiety C and a fatty acid moiety D. The peptide portion A preferably comprises the peptide having SEQ ID NO: 1, having an oxidized or a non-oxidized methionine, and is bound, via its N-terminus to linker portion B. Linker portion B comprises a linker, as defined by $R_4$, preferably a succinate moiety. Glycerol moiety C is bound to linker moiety B and fatty acid moiety D. Fatty acid moiety D comprises 2 fatty acids, having saturated alkyl chains, wherein $R_1$ and $R_2$ are each alkyl chains having between 13 and 19 carbon atoms, preferably 15 carbon atoms.

Optionally, the methionine may be present in its oxidized form, in the form of methionine sulfoxide as shown in FIGS. 2A-2E.

Liposomes:

Liposomes comprising the modified targeting peptides can comprise, in addition to the modified targeting peptide, a phospholipid. Preferably, the phospholipid is a phosphatidylcholine. Optionally, the phosphatidylcholine comprises fatty acid groups having between 14 and 20 carbon atoms. Preferably, the phospholipid has a saturated fatty acid moiety. The phospholipid may comprise one or more than one of: 1,2-Dioleoyl-sn-glycero-3-phosphocholine (DOPC); 1,2-Dipalmitoyl-sn-glycero-3-phosphocholine (DPPC); 1,2-Dilauroyl-sn-glycero-3-phosphocholine (DLPC); 1,2-Dimyristoyl-sn-glycero-3-phosphocholine (DMPC); and 1,2-diheptanoyl-sn-glycero-3-phosphocholine (DHPC). The phospholipid is preferably 1,2-distearoyl-sn-glycero-3-phosphocholine (DSPC). Liposomes may also comprise cholesterol.

Liposomes may contain phospholipid and cholesterol, wherein the phospholipid is preferably DSPC in a molar ratio of between 3:1 and 1:1, phospholipid:cholesterol. Preferably, liposomes contain phospholipid and cholesterol, preferably DSPC in a molar ratio of 2:1. Liposomes may contain the modified targeting peptide in a molar percentage of 0.05% to 5%, relative to the content of cholesterol and phospholipid.

Liposomes may be prepared using the following general method:

A solution of a phospholipid and modified targeting peptide is prepared. The solution is then combined with a solution of cholesterol. The organic lipid solutions are added to the aqueous buffer. The liposome mixture is then extruded using a series of membranes between 400 nanometers (nm) down to 100 nm. This is followed by buffer change and removal of organic solvents by tangential flow filtration (TFF). The liposomes are incubated with a drug to form drug-containing liposomes. Excess drug not bound by the liposome is removed through a second buffer exchange by TFF.

According to an embodiment the phospholipid solution and cholesterol solution are solutions having an alcohol as a solvent. Optionally, the phospholipid solution is a solution in which ethanol is the solvent. Optionally, the cholesterol solution is a solution in which isopropanol is a solvent. Optionally, the buffer solution is an ammonium sulfate buffer. Optionally, the solution is heated to between 50-70° C.

According to an embodiment, the liposomes formed are multilamellar liposomes.

According to an embodiment, the liposome is free of phospholipids having unsaturated fatty acid moieties. According to an embodiment, the liposome is free of 1,2-dioleoyl-sn-glycero-3-phosphocholine (DOPC). According to an embodiment, the liposome is free of 1,2-palmitoyl-phosphatidic acid (DPPA).

Encapsulated Drug:

The liposome may encapsulate or otherwise bind, by non-covalent bonds, a drug or a plurality of drugs.

According to an embodiment, the drug is a hydrophobic drug. According to an embodiment, the drug is a hydrophilic drug.

According to an embodiment, the ratio of drug to phospholipid in the liposome is between 0.1% to 50% by mole.

According to an embodiment, the drug is a biological drug. Optionally, the drug is an anti-cancer drug, a gene or a fragment thereof, siRNA, a plasmid containing a gene therapy or a gene producing drug or a specific toxin against a disease, an antisense DNA, a peptide, a protein, or a protein fragment. According to an embodiment, the drug comprises an alkaloid, an alkylating agent, an anti-tumor antibiotic, an antimetabolite, a hormone and hormone analog, immunomodulator, photosensitizing agent, antibody, peptide, anti-mitotic agent, or a radiotherapeutic agent. In another embodiment, a composition as described herein comprises a plant alkaloid.

According to an embodiment, the liposome's diameter is between 50 nm to 300 nm. In another embodiment, the liposome's diameter is between 50 nm to 200 nm. In another embodiment, the liposome's diameter is between 50 nm to 150 nm. In another embodiment, the liposome's diameter is between 90 nm to 140 nm. In another embodiment, the composition comprises a plurality of liposomes having a mean diameter between 50 nm to 300 nm. In another embodiment, the composition comprises a plurality of liposomes having a mean diameter between 50 nm to 200 nm. In another embodiment, the composition comprises a plurality of liposomes having a mean diameter between 50 nm to 150 nm. In another embodiment, the composition comprises a plurality of liposomes having a mean diameter between 50 nm to 250 nm. In another embodiment, the composition comprises a plurality of liposomes having a mean diameter between 90 nm to 200 nm.

According to an embodiment, the zeta potential of a liposome is from 0 millivolt (mV) to −100 mV. In another embodiment, the zeta potential of a liposome is from −10 mV to −40 mV. In another embodiment, the zeta potential of a liposome is from 0 mV to +100 mV. In another embodiment, the zeta potential of a liposome is from +10 to +40. mV.

Advantages of Modified Targeting Peptides:

Modified targeting peptides described herein are based on modifications of a peptide having an amino acid sequence of SEQ ID NO: 1. The unique modifications described herein provide advantageous qualities to liposomes formed comprising the described modified targeting peptides. Such enhanced qualities include, but are not limited to, increased stability relative to peptides and/or liposomes described in the prior art. The liposomes tend to maintain size and zeta potential over time. Additional advantages include lack of formation of aggregates over time, and suspension uniformity over time.

SEQ ID NO: 1 has been described in U.S. Pat. No. 9,655,848, incorporated herein by reference. Without being bound by theory, it is suggested that peptides having SEQ ID NO: 1 act as blood brain barrier recognition peptides which, when incorporated in modified targeting peptides described herein, in liposomes described herein, facilitate penetration of the liposome to the brain from the circulatory system, when administered to a mammal. Preferably, administration of the liposome to the mammal does not harm the integrity of the BBB by modifying its permeability to agents not associated with liposomes. Preferably, modified targeting peptides described herein have little to no immunogenicity when administered to mammals.

Whereas U.S. Pat. No. 9,655,848 describes conjugated short peptides incorporating SEQ ID NO: 1, only unsaturated conjugated short peptides are described, for example, 1,2-dioleoyl-sn-glycero-3-succinate-A-H—R-E-R-M-S—COOH. It has been found that such conjugated short peptides are less stable than modified targeting peptides described herein. Reducing agents may need to be added to such conjugated short peptides having unsaturated peptides, in order to increase stability. On the other hand, modified targeting peptides described herein are stable without addition of reducing agents.

Methods for Treatment:

Some embodiments relate to methods for treating a disease comprising administering to a patient in need thereof, a therapeutically effective amount of a liposome described herein. The therapeutically effective amount may be an amount, which upon administration to a patient, ameliorates a symptom associated with the disease or modifies the level of a biological marker associated with the disease in the patient.

According to an embodiment, the method for administration of a liposome is through a parenteral route. Optionally, the route of administration is intranasal administration. Optionally, the route is injection, via intravenous, subcutaneous or intramuscular routes.

According to an embodiment, the drug is administered in a liposome to treat a disease or pathology of the central nervous system (CNS). The disease or pathology of the brain may be selected from the group consisting of: trauma, infections, neurodegeneration, movement disorders, autoimmune CNS indications, Stroke, ADHD, autism and addiction. Such a drug is a brain therapeutic compound having an established therapeutic effect within the brain. According to an embodiment, the brain disease or pathology is selected from the group comprising: acoustic neuroma, acquired brain injury, agenesis corpus callosum, Alzheimer's disease, amyotrophic lateral diseases, aneurysm, aphasia, arteriovenous malformation, batten disease, Behçet's disease, blepharospasm, brain tumor, brain cancer, cerebral lupus, cerebral palsy, cervical dystonia, Charcot-Marie-Tooth disorder, Chiari malformation, chronic inflammatory demyelinated polyneuropathy, coma and persistent vegetative state, concussion, Creutzfeldt-Jakob disease, dementia (non-Alzheimer type), depression, Down syndrome, dysautonomia, dyslexia, dyspraxia, dystonia, encephalitis, epilepsy, essential tremor, Friedreich's ataxia, Gaucher disease, Guillain-Barre syndrome, Huntington's disease, hydrocephalus, intracranial hypertension, leukodystrophy, Meniere's disease, meningitis, meningococcal disease, migraine, motor neuron disease, multiple sclerosis, muscular dystrophy, myasthenia gravis, narcolepsy, Parkinson's disease, peripheral neuropathy, Prader-Willi syndrome, progressive supranuclear palsy, restless legs syndrome, Rett syndrome, Shy Drager syndrome, sleep disorders, spasmodic dysphonia, stroke, subarachnoid hemorrhage, Sydenham's chorea, Tay-Sachs disease, Tourette syndrome, transient ischemic attack, transverse myelitis, trigeminal neuralgia, tuberous sclerosis, glioblastoma, neuropathic pain, traumatic brain injury, von-Hippel-Lindau syndrome, a neuroimmune disorder, and a psychiatric disease.

Optionally, the disease is brain cancer, optionally selected from a primary tumor (a tumor originating in the brain) or a secondary tumor (originating from outside of the brain). Optionally, the brain cancer is selected from the group consisting of: a glioma, a craniopharyngioma, a lymphoma, a hemangioblastoma, a meningioma, acoustic neuroma/neurinoma, and a pituitary tumor.

According to an embodiment, the amount of liposome administered to a patient in need thereof contains within it the amount of drug equivalent to an approved dosage of the drug for a given indication. Optionally, the amount of liposome administered to a patient in need thereof contains within it less than the equivalent amount of the drug approved for a given indication. Optionally, the amount of liposome administered to a patient in need thereof contains within it between about 0.1% and 50% of the equivalent amount of the drug approved for a given indication.

The following examples are provided to illustrate certain particular features and/or embodiments. These examples should not be construed to limit the disclosure to the particular features or embodiments described.

EXAMPLES

Example 1A

Preparation of a Modified Targeting Peptide

A modified targeting peptide wherein $R_1$ and $R_2$ are each $C_{15}H_{31}$, and $R_5$ is $(CH_2)_2$, and $R_6$ and $R_7$ are each carbonyl, was prepared according to the synthesis described below.

The peptide moiety, according to SEQ ID NO:1, was prepared in protected form, by Atlantic Peptide. Protected form included modifications to Histidine (trityl protection), Arginine (2,2,4,6,7-Pentamethyldihydrobenzofuran-5-sulfonyl), Glu (tert-Butyl), and Serine (tert-Butyl).

Step 1

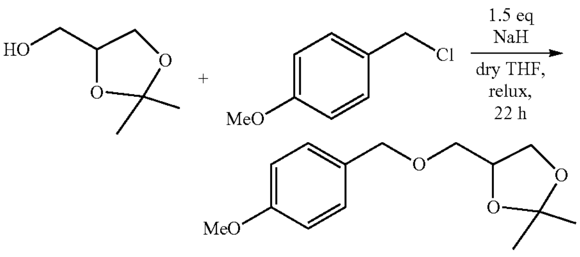

(1)

Compound (1) was prepared as described in: Ana Gil-Mesón et al. molecules 2016, 21, 47. Briefly, DL-1,2-isopropylideneglycerol, was added 4-methoxybenzyl chloride in the presence of sodium hydride and potassium iodide in tetrahydrofuran (THF). The reaction mixture was heated at reflux (66° C.), for 16-24 hours (h) to yield crude compound (1) 3-methoxybenzyl-1,2-isopropylideneglycerol.

Step 2

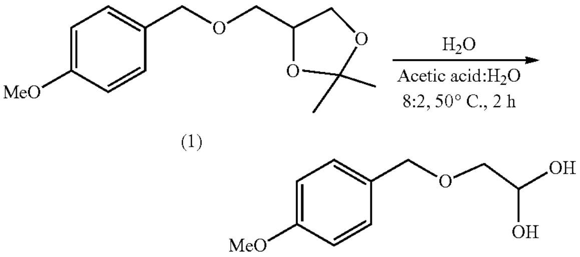

(1)

(2)

Compound (2) was prepared as described in Masato Abe et al. *Biochemistry* 2011, 8383. Compound (1) (3-methoxybenzyl-1,2-isopropylideneglycerol), was reacted with acetic acid/water. The reaction mixture was heated for 2 h at 50° C. to yield crude (2), 1-p-methoxybenzylglycerol.

Step 3

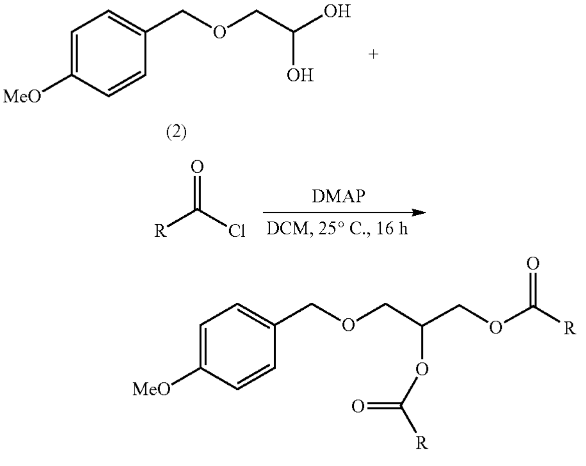

(2)

(3)

$R = C_{15}H_{31}$

Compound (3) was prepared as described in Masato Abe et al. *Biochemistry* 2011, 8383. Compound (2), 1-p-methoxybenzylglycerol, palmitoyl chloride, pyridine and 4-(dimethylamino)pyridine (DMAP) in dichloromethane (DCM) were kept at room temperature overnight to yield compound (3), 1-methoxybenzyl-2,3-dipalmitoylglycerol. The overall yield for steps 1-3 was 36%.

Step 4

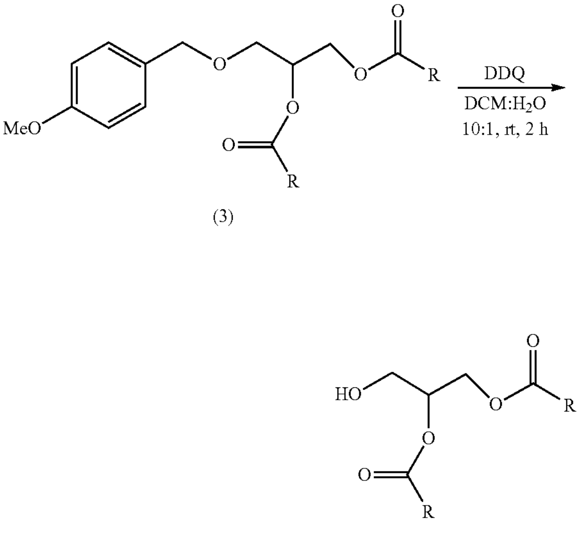

(3)

(4)

$R = C_{15}H_{31}$

Compound (4) was prepared as described in Stuart, J. Conway et al. *Org. Biomol. Chem.* 2010, 66. Compound (3) 1-methoxybenzyl-2,3-dipalmitoylglycerol and 2,3-dichloro-5,6-dicyano-p-benzoquinone (DDQ) dichloromethane (DCM)/water were reacted at room temperature to yield compound (4), 1,2-dipalmitoylglycerol, at a yield of 63%.

Step 5

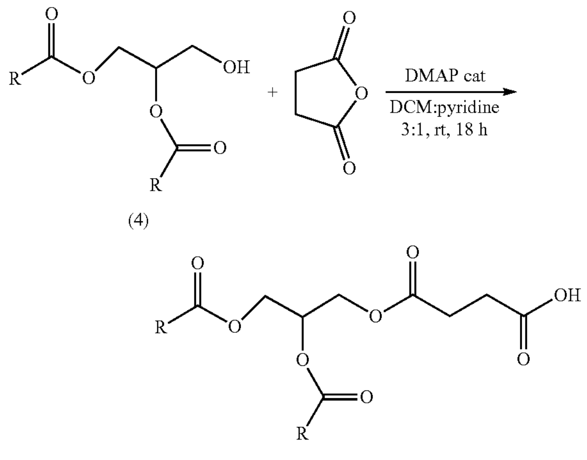

(4)

(5)

R = $C_{15}H_{31}$

Compound (5) was prepared as described in R. K. Gain et al. *Chemistry and Physics of Lipids* (1986), 237. Compound (4), 1,2-dipalmitoylglycerol, succinic anhydride and 4-(dimethylamino)pyridine were added to pyridine and dichloromethane (DCM). The reaction mixture was kept at room temperature overnight, to yield compound (5), 1-succinyl-2,3-dipalmitoylglycerol in a yield of 85%.

Step 6

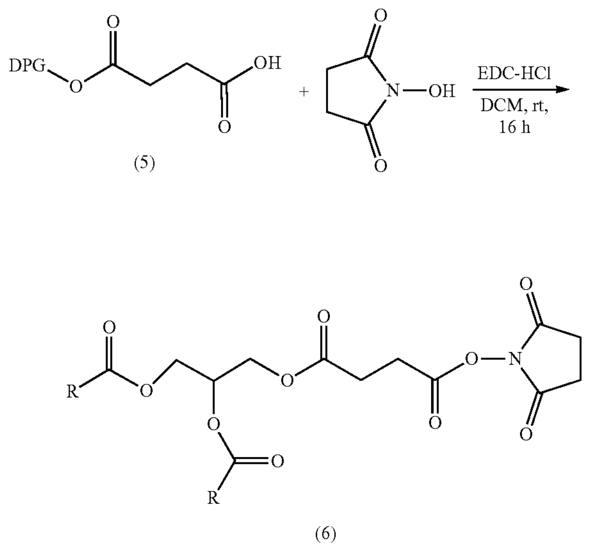

(5)

(6)

DPG: dipalmitoylglyceryl

R = $C_{15}H_{31}$

Compound (6) was prepared as described in Ralph Moser et al. *J. Org. Chem.* (2012), 3143. Compound (5), 1-succinyl-2,3-dipalmitoylglycerol, N-(3-dimethylaminopropyl)-N'-ethylcarbodiimide hydrochloride, (EDC-HCl) and N-hydroxysuccinimide in DCM were stirred at room temperature for overnight, to yield compound (6), 2,3-dipalmitoylglyceryl-1-succinylsuccinimide, in an 89% yield.

Step 7

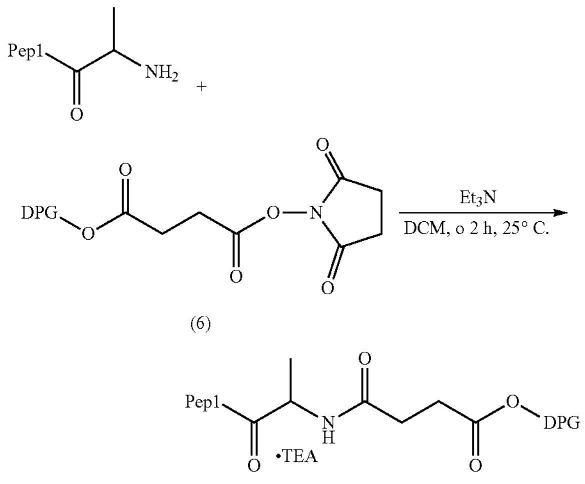

(6)

(7)

Pep1: NH-His(Trt)-Arg(Pbf)-Glu(OtBu)-Arg(Pbf)-Met-Ser(tBu)-Acid

DPG-dipalmitoylglyceryl

Compound (7) was prepared as described in Unger Evan, C. et al. PCT Application Publication WO 02/36161 A2; 2002. Compound (6), 2,3-dipalmitoylglyceryl-1-succinylsuccinimide, peptide NH2-Ala-His(Trt)-Arg(Pbf)-Glu(OBu)-Arg (Pbf)-Met-Ser(tBu)-OH, and triethylamine in dichloromethane were mixed for 2 h at room temperature to yield compound (7), 2,3-dipalmitoylglyceryl-1-succinyl-NH-Ala-His(Trt)-Arg(Pbf)-Glu(OtBu)-Arg(Pbf)-Met-Ser(tBu)-OH.

Step 8

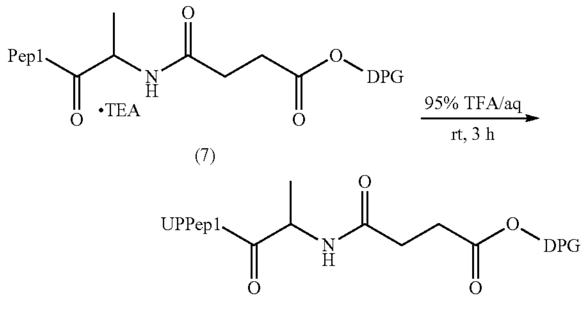

(7)

(8)

Pep1: NH-His(Trt)-Arg(Pbf)-Glu(OtBu)-Arg(Pbf)-Met-Ser(tBu)-Acid

DPG: dipalmitoylglyceryl

UPPep1 (Unprotectet peptide 1): NH-His-Arg-Glu-Arg-Met-Ser-Acid

Compound (8): 2,3-Dipalmitoylglyceryl-1-succinyl-NH-Ala-His-Arg-Glu-Arg-Met-Ser-OH Compound (8) was prepared as described in Tor W. Jensen et al. *J. Am. Chem. Soc.*, 2004, 15223. Compound (7), 2,3-dipalmitoylglyceryl-1-succinyl-NH-Ala-His(Trt)-Arg (Pbf)-Glu(OtBu)-Arg(Pbf)-Met-Ser(tBu)-OH, was treated with trifluoracetic acid (TFA)/water to yield compound (8), 2,3-dipalmitoylglyceryl-1-succinyl-NH-Ala-His-Arg-Glu-Arg-Met-Ser-OH. The yield of steps 7 and 8 was 60%. The methionine residue was partially oxidized. See FIG. 2A.

Example 1B

Preparation of a Modified Targeting Peptide

A modified targeting peptide wherein $R_1$ and $R_2$ are each $C_{15}H_{31}$, $R_5$ is $(CH_2)_3$, and $R_6$ and $R_7$ are each carbonyl, was prepared according to the synthesis described below. Steps 1-4 were performed as in example 1A.

Step 5

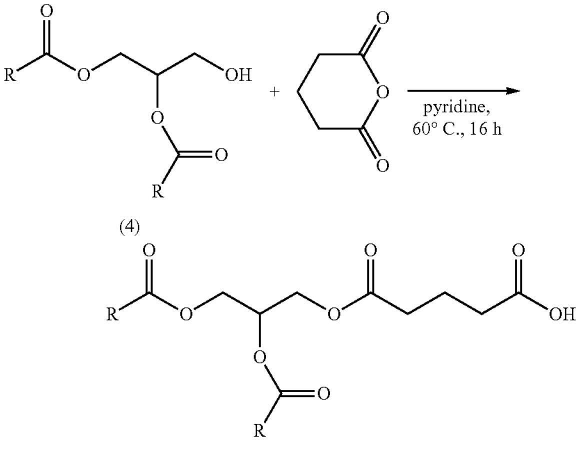

(4)

(9)

R = $C_{15}H_{31}$

Compound (9) was prepared as described in R. K. Gain et al. *Chemistry and Physics of Lipids* (1986), 237. Compound (4), 1,2-dipalmitoylglycerol and glutaric anhydride were added to pyridine. The reaction mixture was heated at 60° C. overnight to yield compound (9), 1-glutaryl-2,3-dipalmitoylglycerol at a yield of 64%.

Step 6

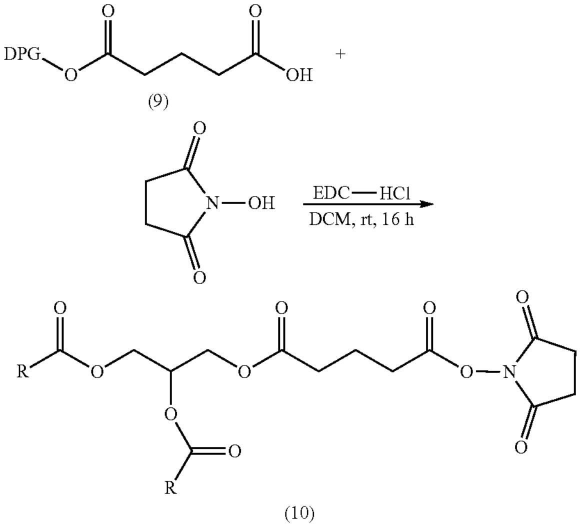

(9)

(10)

R = $C_{15}H_{31}$

Compound (10) was prepared as described in Ralph Moser et al. *J. Org. Chem.* (2012), 3143. Compound (9), 1-glutaryl-2,3-dipalmitoylglycerol, N-(3-dimethylaminopropyl)-N'-ethylcarbodiimide hydrochloride, (EDC-HCl) and N-hydroxysuccinimide in dichloromethane (DCM) were stirred at room temperature overnight to yield compound (10), 2,3-dipalmitoylglyceryl-1-glutarylsuccinimide, at a yield of 55%.

Step 7

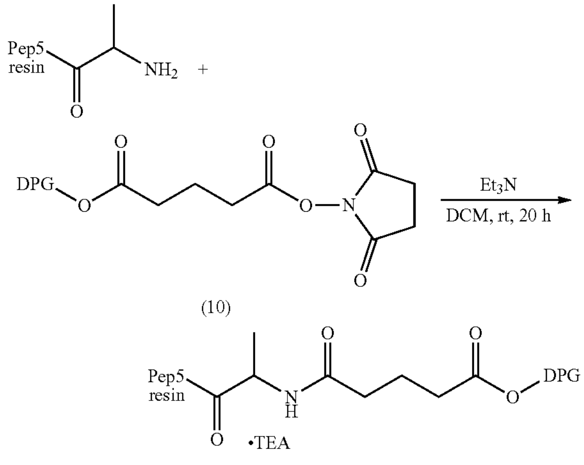

(10)

(11)

DPG: dipalmitoylglyceryl

Pep5 resin: NH-His(Trt)-Arg(Pbf)-Glu(OtBu)-Arg(Pbf)-Met-Ser(tBu)-2-chlorotrityl resin Compound (11) was prepared as described in Tor W. Jensen et al. *J. Am. Chem. Soc.,* 2004, 15223. Compound (10), 2,3-dipalmitoylglyceryl-1-glutarylsuccinimide, peptide NH2-Ala-His(Trt)-Arg(Pbf)-Glu(OBu)-Arg(Pbf)-Met-Ser(tBu)-2-chlorotrityl resin, and triethylamine were mixed in dichloromethane for 16 h at room temperature to yield compound (11), 2,3-dipalmitoylglyceryl-1-glutaryl-NH-Ala-His(Trt)-Arg(Pbf)-Glu(OtBu)-Arg(Pbf)-Met-Ser(tBu)-2-chlorotrityl resin.

Step 8

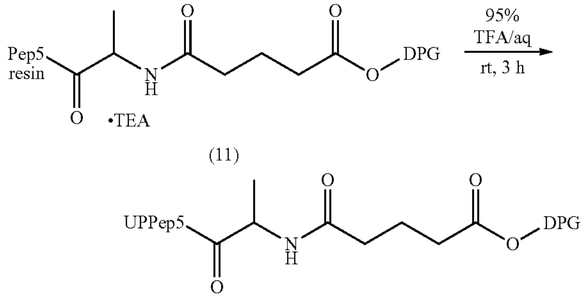

(11)

(12)

DPG: dipalmitoylglyceryl

Pep5 resin: NH-His(Trt)-Arg(Pbf)-Glu(OtBu)-Arg(Pbf)-Met-Ser(tBu)-2-chlorotrityl resin UPPep5 (Unprotectet peptide 5): NH-His-Arg-Glu-Arg-Met-Ser Acid Compound (12): 2,3-Dipalmitoylglyceryl-1-glutaryl-NH-Ala-His-Arg-Glu-Arg-Met-Ser-OH Compound (12) was prepared as described in Tor W. Jensen et al. *J. Am. Chem. Soc.,* 2004, 15223. Compound (11), 2,3-dipalmitoylglyceryl-1-glutaryl-NH-Ala-His(Trt)-Arg(Pbf)-Glu(OtBu)-Arg(Pbf)-Met-Ser(tBu)-2-chlorotrityl resin, was treated with trifluoracetic acid (TFA)/water to yield compound (12), 2,3-dipalmitoylglyceryl-1-glutaryl- NH-Ala-His-Arg-Glu-Arg-Met-Ser-OH. The overall yield of steps 7 and 8 was 24%. The methionine residue was partially oxidized. See FIG. 2B.

Example 1C

Preparation of a Modified Targeting Peptide

A modified targeting peptide wherein $R_1$ and $R_2$ are each $C_{15}H_{31}$, $R_5$ is $CH_2$—$C(CH_3)_2$—$CH_2$, and $R_6$ and $R_7$ are each carbonyl, was prepared according to the synthesis described below. Steps 1-4 were performed as in example 1A.

Step 5

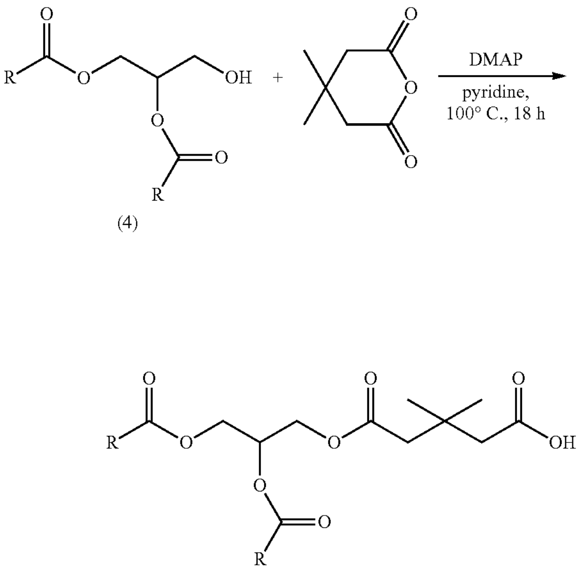

(4)

(13)

R = $C_{15}H_{31}$

Compound (13) was prepared as described in Sun, 1-Chen et al. *J. Med. Chem* (1998), 41(23), 4648-4657. Compound (4), 1,2-dipalmitoylglycerol, 4-(dimethylamino)pyridine and 3,3-dimethylglutaric anhydride were added to pyridine. The reaction mixture was heated at 100° C. overnight to yield compound (13), 1-(3',3'-dimethylglutaryl)-2,3-dipalmitoylglycerol at a yield of 50%.

Step 6

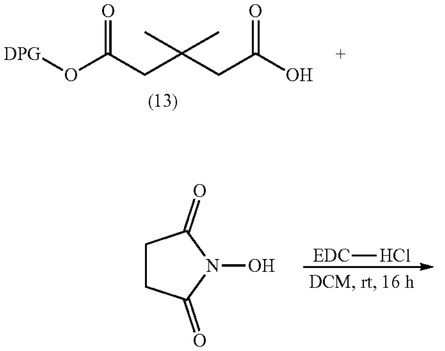

(13)

-continued

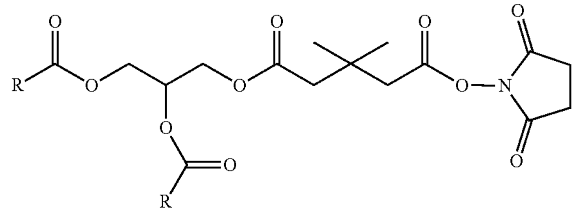

(14)

DPG: dipalmitoylglyceryl

R = $C_{15}H_{31}$

Compound (14) was prepared as described in Ralph Moser et al. *J. Org. Chem.* (2012), 3143. Compound (13), 1-(3',3'-dimethylglutaryl)-2,3-dipalmitoylglycerol, N-(3-dimethylaminopropyl)-N'-ethylcarbodiimide hydrochloride, (EDC-HCl) and N-hydroxysuccinimide in dichloromethane (DCM) were stirred at room temperature overnight, to yield compound (14), 2,3-dipalmitoylglyceryl-1-(3',3'-dimethylglutaryl)succinimide, at a 32% yield.

Step 7

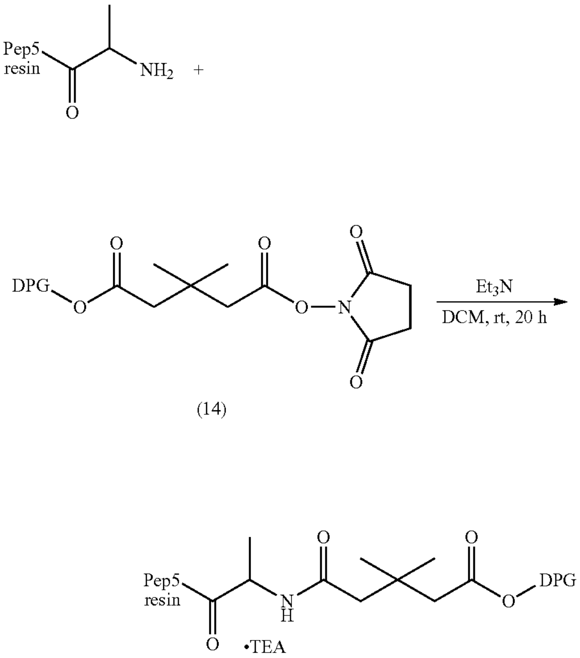

(14)

(15)

DPG: dipalmitoylglyceryl

Pep5 resin: NH-His(Trt)-Arg(Pbf)-Glu(OtBu)-Arg(Pbf)-Met-Ser(tBu)-2-chlorotrityl resin Compound (15) was prepared as described in Tor W. Jensen et al. *J. Am. Chem. Soc.,* 2004, 15223. Compound (14), 2,3-dipalmitoylglyceryl-1-(3',3'-dimethylglutaryl)succinimide, peptide NH2-Ala-His(Trt)-Arg(Pbf)-Glu(OBu)-Arg (Pbf)-Met-Ser(tBu)-2-chlorotrityl resin, and triethylamine were mixed in dichloromethane for 16 h at room temperature to yield compound (15), 2,3-dipalmitoylglyceryl-1-(3',3'-dimethylglutaryl)-NH-Ala-His(Trt)-Arg(Pbf)-Glu (OtBu)-Arg(Pbf)-Met-Ser(tBu)-2-chlorotrityl resin.

Step 8

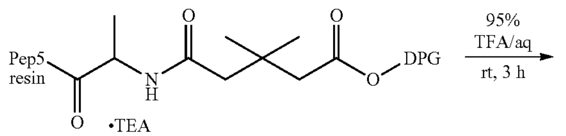

(15)

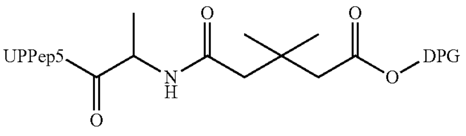

(16)

DPG: dipalmitoylglyceryl
Pep5 resin: NH-His(Trt)-Arg(Pbf)-Glu(OtBu)-Arg(Pbf)-Met-Ser(tBu)-2-chlorotrityl resin
UPen5 (Unprotectet peptide 5): NH-His-Arg-Met-Ser-Acid
Compound (16): 2,3-Dipalmitoylglyceryl-1-dimethylglutaryl-NH-Ala-His-Arg-Glu-Arg-Met-Ser-OH Compound (16) was prepared as described in Tor W. Jensen et al. *J. Am. Chem. Soc.,* 2004, 15223. Compound (15), 2,3-dipalmitoylglyceryl-1-(3',3'-dimethylglutaryl)-NH-Ala-His(Trt)-Arg(Pbf)-Glu(OtBu)-Arg(Pbf)-Met-Ser(tBu)-2-chlorotrityl resin, was treated with trifluoracetic acid (TFA)/water to yield compound (16), 2,3-dipalmitoylglyceryl-1-(3',3'-dimethylglutaryl)-NH-Ala-His-Arg-Glu-Arg-Met-Ser-OH. The overall yield of steps 7 and 8 was 40%. The methionine residue was partially oxidized. See FIG. 2C.

Example 1D

Preparation of a Modified Targeting Peptide

A modified targeting peptide wherein $R_1$ and $R_2$ are each $C_{15}H_{31}$, $R_5$ is $(CH_2)_6$, and $R_6$ and $R_7$ are each carbonyl, was prepared according to the synthesis described below. Steps 1-4 were performed as in example 1A.

Step 5

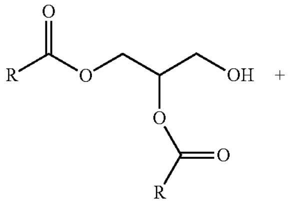

(4)

$HCO_2(CH_2)_6CO_2H$ suberic acid

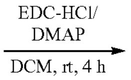

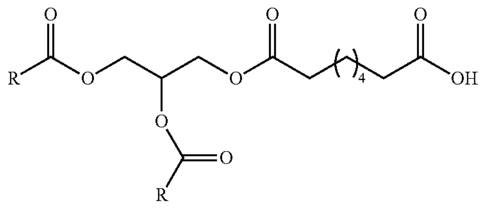

(17)

R = $C_{15}H_{31}$

Compound (17) was prepared as described in Baryza, J. L. et al. 2014, WO 2014/136086 A1. Compound (4), 1,2-dipalmitoylglycerol, suberic acid, N-(3-dimethylaminopropyl)-N'-ethylcarbodiimide hydrochloride, (EDC-HCl), and 4-(dimethylamino)pyridine in dichloromethane (DCM) were stirred at room temperature for 4 h to yield compound (17), 1-suberyl-2,3-dipalmitoylglycerol at a yield of 24%.

Step 6

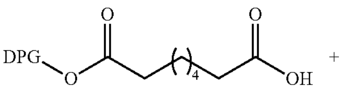

(17)

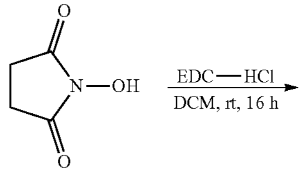

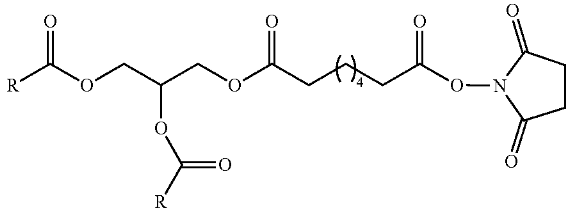

(18)

DPG: dipalmitoylglyceryl

R = $C_{15}H_{31}$

Compound (18) was prepared as described in Ralph Moser et al. *J. Org. Chem.* (2012), 3143. Compound (17), 1-suberyl-2,3-dipalmitoylglycerol, N-(3-dimethylaminopropyl)-N'-ethylcarbodiimide hydrochloride, (EDC-HCl) and N-hydroxysuccinimide in dichloromethane (DCM) were stirred at room temperature overnight, to yield compound (18), 2,3-dipalmitoylglyceryl-1-suberylsuccinimide, at a 23% yield.

Step 7

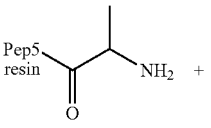

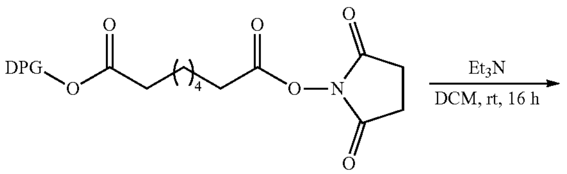

(18)

-continued

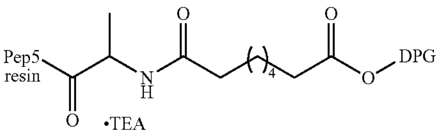

(19)

DPG: dipalmitoylglyceryl
Pep5 resin: NH-His(Trt)-Arg(Pbf)-Glu(OtBu)-Arg(Pbf)-Met-Ser(tBu)-2-chlorotrityl resin Compound (19) was prepared as described in Tor W. Jensen et al. *J. Am. Chem. Soc.,* 2004, 15223. Compound (18), 2,3-dipalmitoylglyceryl-1-suberylsuccinimide, peptide NH2-Ala-His(Trt)-Arg(Pbf)-Glu(OBu)-Arg(Pbf)-Met-Ser(tBu)-2-chlorotrityl resin, and triethylamine were mixed in dichloromethane for 16 h at room temperature to yield compound (19), 2,3-dipalmitoylglyceryl-1-suberyl-NH-Ala-His(Trt)-Arg(Pbf)-Glu(OtBu)-Arg(Pbf)-Met-Ser(tBu)-2-chlorotrityl resin.

Step 8

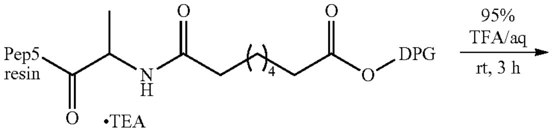

(19)

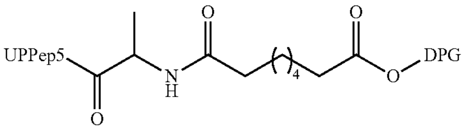

(20)

DPG: dipalmitoylglyceryl
Pep5 resin: NH-His(Trt)-Arg(Pbf)-Glu(OtBu)-Arg(Pbf)-Met-Ser(tBu)-2-chlorotrityl resin
UPPep5 (Unprotectet peptide 5): NH-His-Arg-Glu-Arg-Met-Ser-Acid
Compound (20): 2,3-Dipalmitoylglyceryl-1-suberyl-NH-Ala-His-Arg-Glu-Arg-Met-Ser-OH Compound (20) was prepared as described in Tor W. Jensen et al. *J. Am. Chem. Soc.,* 2004, 15223. Compound (19), 2,3-dipalmitoylglyceryl-1-suberyl-NH-Ala-His(Trt)-Arg(Pbf)-Glu(OtBu)-Arg(Pbf)-Met-Ser(tBu)-2-chlorotrityl resin, was treated with trifluoracetic acid (TFA)/water to yield compound (20), 2,3-dipalmitoylglyceryl-1-suberyl-NH-Ala-His-Arg-Glu-Arg-Met-Ser-OH. The overall yield of steps 7 and 8 was 12%. The methionine residue was partially oxidized. See FIG. 2D.

Example 1E

Preparation of a Modified Targeting Peptide

A modified targeting peptide wherein $R_1$ and $R_2$ are each $C_{15}H_{31}$, and $R_5$ is $CH_2$, $R_6$ is a bond and $R_7$ is carbonyl, was prepared according to the synthesis described below. Steps 1-4 were performed as in example 1A.

Step 5

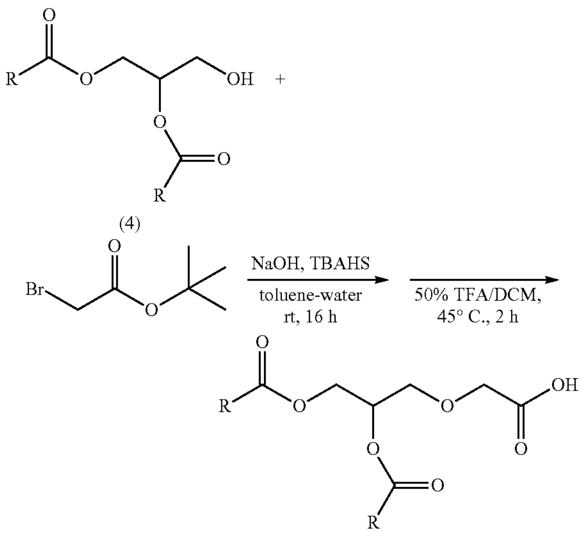

(4)

(21)

$R = C_{15}H_{31}$

Compound (21) was prepared as described in Baryza, J. L. et al. 2014, WO 2014/136086 A1 and as described in Cheaib et al. *Tetrahedron: Asymetry* (2008), 19(16), 1919-1933. Compound (4), 1,2-dipalmitoylglycerol, tert-butyl bromoacetate, sodium hydroxide, and tetrabutylammonium hydrogensulfate in toluene-water were stirred at room temperature for 16 h to give tert-butyl ester intermediate, which was stirred in TFA/DCM at 45° C. for 2 h to yield compound (21), 1-acetyl-2,3-dipalmitoylglycerol at a yield of 27%.

Step 6

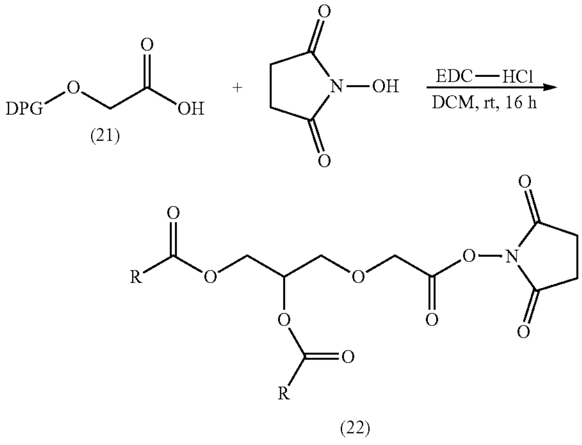

(21)

(22)

$R = C_{15}H_{31}$

Compound (22) was prepared as described in Ralph Moser et al. *J. Org. Chem.* (2012), 3143. Compound (21), 1-acetyl-2,3-dipalmitoylglycerol, N-(3-dimethylaminopropyl)-N'-ethylcarbodiimide hydrochloride, (EDC-HCl) and N-hydroxysuccinimide in dichloromethane (DCM) were stirred at room temperature overnight, to yield compound (22), 2,3-dipalmitoylglyceryl-1-acetylsuccinimide, at a 50% yield.

Step 7

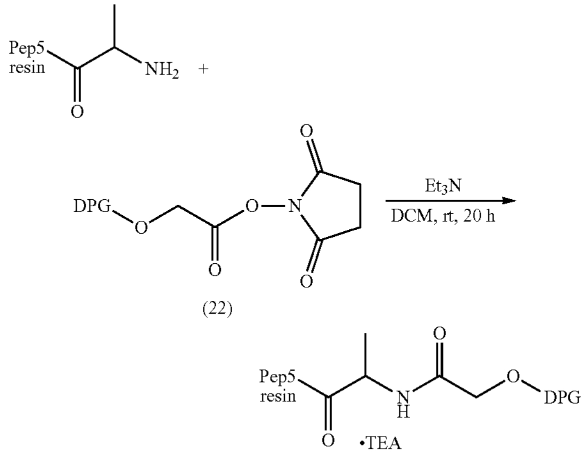

(22)

(23)

DPG: dipalmitoylglyceryl
Pep5 resin: NH-His(Trt)-Arg(Pbf)-Glu(OtBu)-Arg(Pbf)-Met-Ser(tBu)-2-chlorotrityl resin Compound (23) was prepared as described in Tor W. Jensen et al. *J. Am. Chem. Soc.,* 2004, 15223. Compound (22), 2,3-dipalmitoylglyceryl-1-acetylsuccinimide, peptide NH2-Ala-His(Trt)-Arg(Pbf)-Glu(OBu)-Arg(Pbf)-Met-Ser(tBu)-2-chlorotrityl resin, and triethylamine were mixed in dichloromethane for 16 h at room temperature to yield compound (23), 2,3-dipalmitoylglyceryl-1-acetyl-NH-Ala-His(Trt)-Arg(Pbf)-Glu(OtBu)-Arg(Pbf)-Met-Ser(tBu)-2-chlorotrityl resin.

Step 8

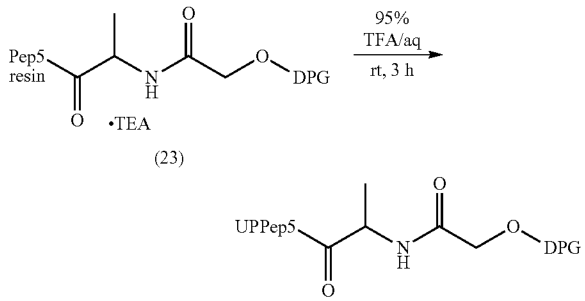

(23)

(24)

DPG: dipalmitoylglyceryl
Pep5 resin: NH-His(Trt)-Arg(Pbf)-Glu(OtBu)-Arg(Pbf)-Met-Ser(tBu)-2-chlorotrityl resin
UPPep5 (Unprotectet peptide 5): NH-His-Arg-Glu-Arg-Met-Ser-Acid
Compound (24): 2,3-Dipalmitoylglyceryl-1-acetyl-NH-Ala-His-Arg-Glu-Arg-Met-Ser-OH Compound (24) was prepared as described in Tor W. Jensen et al. *J. Am. Chem. Soc.,* 2004, 15223. Compound (23), 2,3-dipalmitoylglyceryl-1-acetyl-NH-Ala-His (Trt)-Arg (Pbf)-Glu(OtBu)-Arg(Pbf)-Met-Ser(tBu)-2-chlorotrityl resin, was treated with trifluoracetic acid (TFA)/water to yield compound (24), 2,3-dipalmitoylglyceryl-1-acetyl-NH-Ala-His-Arg-Glu-Arg-Met-Ser-OH. The overall yield of steps 7 and 8 was 7%. The methionine residue was partially oxidized. See FIG. 2E.

Example 2

Preparation of Liposomes Using Modified Targeting Peptides.

The liposomes were prepared by conventional injection method (S. Batzri and E. D. Korn, Biochim. Biophys. Acta 298, 1015 (1973). Briefly, a solution of DSPC, cholesterol and the modified targeting peptide, example 1A, in an organic alcohol (ethanol or IPA) was added at 60° C. to a solution of ammonium sulphate. The liposome solution was extruded at 65° C. through polycarbonate membranes having 200 nm and then 100 nm pores, under pressure of 150 psi to 50 psi, 5 times per each membrane. The organic solvent and the buffer were exchanged with MES buffer, 0.002M, pH=6.5, 8% sucrose using TFF. The TFF was performed using a KrosFlo system and a Hollow Fiber of 20 $cm^2$. The MES buffer containing 8% sucrose acted as the ionic pump. The molar ratio of Cholesterol to DSPC was 2:1. The amount of modified targeting peptide was 0.5% (molar percentage) relative to the combined amount of cholesterol and phospholipid.

Example 3: Loading of Liposomes

The loading of doxorubicin hydrochloride was done conventional ways described in the literature (Zucker D, Marcus D, Barenholz Y, et al. Liposome drugs' loading efficiency: a working model based on loading conditions and drug's physicochemical properties. J Control Release 2009; 139: 73-80). The mixture of liposomes prepared according to Example 2, were incubated with doxorubicin in MES buffer at 60° C. for 60 minutes and cooled to room temperature. Finally, the MES buffer was exchanged with HEPES buffer, 0.02M HEPES, 0.15M NaCl pH 7.4 using TFF.

Loading was performed with doxorubicin. The amount of doxorubicin relative to the combined amount of cholesterol and phospholipid was 4.1% by molar ratio.

Example 4: Testing of Liposomes—Physical Characteristics

Size, zeta potential and homogeneity of the final loaded liposomes prepared using the procedure described in Example 3 were tested at two time points after preparation and after one month of storage at 2° C. to 8° C. using dynamic light scattering through a Zetasizer device (Malvern Pannalytical.) The stability data at baseline and at one month is shown in Table 1.

TABLE 1

| Liposomes date of preparation: 29.5.19 | | | |
|---|---|---|---|
| Test date | Size(nm) N = 9 | PDI N = 9 | Zeta potential (mV) N = 9 |
| Baseline | 114.7 | 0.11 | −18 |
| 1 Month | 113.1 | 0.12 | −16.8 |

These results indicate that stable liposomes were formed.

Example 5: Testing of Liposomes—Biological Characteristics

A study was performed to determine doxorubicin distribution after administration, when comparing three doxorubicin-containing compositions, each administered to a group of 10 male ICR mice aged 7 weeks. Composition 1 was free doxorubicin. Composition 2 was doxorubicin formulated in liposomes, without modified targeting peptide. Composition 3 was doxorubicin, formulated in liposomes, with a modified targeting peptide, as in example 4.

Animals were administered doxorubicin in the following amount per administration, for each of the three compositions. Composition 1, was administered in HEPES solution at a dose of 7.5 mg/kg, in a volume of 100 microliter (μl) via the intravenous route. Compositions 2 and 3 were each administered at a dose of 15 mg/kg (equivalent of doxorubicin) in a volume of 300 μl via the intravenous route.

Figure 3:
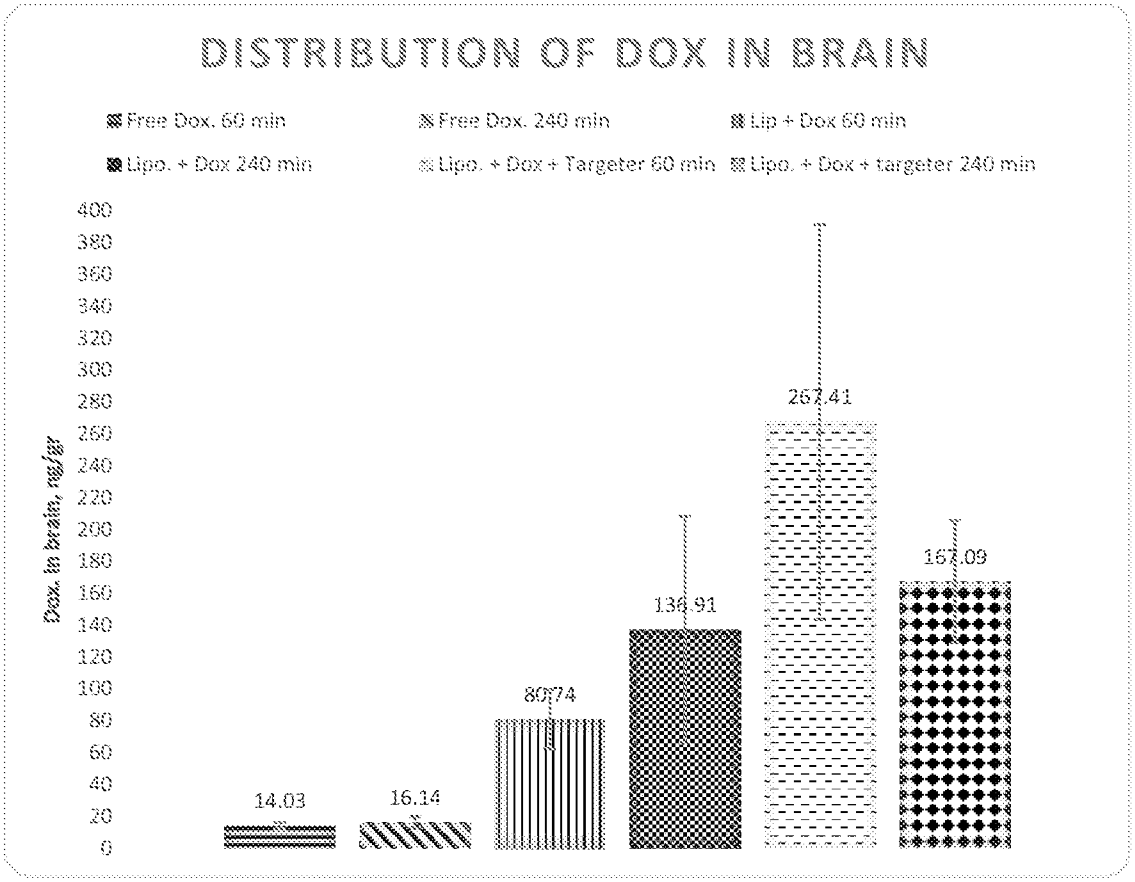
FIG. 3 is a graph showing presence of doxorubicin in brains of animals after administration of doxorubicin in various formulation at two time points following administration (60 minutes and 240 minutes), showing increased brain penetration in animals to which doxorubicin in liposomes having modified targeting peptides was administered.

Five mice in each group were sacrificed one hour post administration, and five mice four hours post administration, and doxorubicin brain concentrations were determined using an LC-MS/MS method. Results of brain concentration associated with administration of Compositions 1, 2 and 3 are shown in a graph in FIG. 3. Composition 1 (labeled "Free dox") provided low brain concentration, both at 60 and 240 minutes post administration. Composition 2 (labeled Lip+Dox) provided higher brain concentrations at 60 minutes relative to composition 1, indicating that liposomes loaded with doxorubicin are more effective in penetration the blood-brain barrier than free doxorubicin. After 240 minutes, the brain concentration of doxorubicin increased relative to 60 minutes. Composition 3 (labeled Lip.+Dox+Targeter) provided higher brain concentrations at 60 minutes relative to compositions 1 and 2 at both time points. This indicates a very rapid penetration of the blood-brain barrier. At 240 minutes, brain concentration decreases relative to composition 3 at 60 minutes. Without being bound by theory, it is suggested that this decrease results from rapid blood-brain barrier penetration, followed by rapid metabolism of doxorubicin in the brain.

These results indicate that modified targeting peptides described herein enhance blood-brain barrier penetration of liposomes and may be used as an effective platform for administering drug-containing liposomes to the brain, thereby providing enhanced effects and/or limiting systemic exposure to the drugs.

Example 6: Preparation of Erlotinib Liposomes

To a hot solution at 60° C. of 790 mg DSPC and 5 mg Erlotinib were added in 3 ml of IPA 193.5 mg of Cholesterol at the same temperature. The combined solution was added quickly into a 0.25M solution of ammonium sulphate. A white suspension of liposomes was formed.

Some embodiments described herein relates to a modified peptide having the structure:

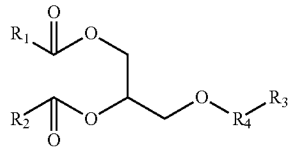

wherein $R_1$ and $R_2$ are each the same or different and are an alkyl chain having between 13 and 19 carbon atoms, $R_3$ is a peptide having a sequence according to SEQ ID NO:1, and wherein $R_4$ is a linker having the structure $R_6$-$R_5$-$R_7$, wherein $R_6$ and $R_7$ are each independently a bond or a carbonyl group; and $R_5$ is selected from the group consisting of: $C_{1-20}$ straight alkyl, $C_{3-20}$ branched alkyl, $C_{3-20}$ cyclic alkyl, and $C_{6-20}$ arylalkyl. Optionally, $R_1$ and $R_2$ are a linear alkyl chain having 15 carbon atoms. Optionally, the peptide is attached to the linker at the N-terminus of the peptide. Optionally, $R_3$ comprises the peptide having a sequence according to SEQ ID NO:1 wherein the methionine residue is oxidized in the form of sulfoxide. Optionally, $R_6$ and $R_7$ are each a carbonyl group. Optionally, $R_6$ is a bond and $R_7$ is a carbonyl group. Optionally, $R_5$ is a $C_{1-20}$ straight alkyl or a $C_{3-20}$ branched alkyl. Optionally, $R_5$ is a $C_{1-6}$ straight alkyl or a $C_{3-6}$ branched alkyl. Optionally, $R_5$ is a $C_2$ straight alkyl. Optionally, $R_5$ is a $CH_2$. Optionally, $R_5$ is a $C_3$ straight alkyl. Optionally, $R_5$ is a $C_6$ straight alkyl. Optionally, $R_5$ is a $CH_2—C(CH_3)_2—CH_2$.

Some embodiments relate to a liposome comprising the modified peptide described above. Optionally, the liposome further comprises a phospholipid and a cholesterol. Optionally, the phospholipid has a saturated fatty acid moiety. Optionally, the phospholipid is 1,2-distearoyl-sn-glycero-3-phosphocholine. Optionally, the molar ratio of phospholipid to cholesterol is between 3:1 and 1:1. Optionally, the molar ratio of phospholipid to cholesterol is 2:1. Optionally, the modified targeting peptide is present in a molar percentage of 0.05% to 5%, relative to the combined amount of cholesterol and phospholipid. Optionally, the modified targeting peptide is present in a molar percentage of 0.5% relative to the combined amount of cholesterol and phospholipid. Optionally, the liposome is free of 1,2-dioleoyl-sn-glycero-3-phosphocholine (DOPC). Optionally, the liposome is free of 1,2-palmitoyl-phosphatidic acid (DPPA). Optionally, the liposome further comprises a drug. Optionally, the drug is a hydrophobic drug. Optionally, the molar ratio of phospholipid to drug is between 1:0.01 and 1:0.1 Optionally, the molar ratio of phospholipid to drug is 1:0.05. Optionally, the drug is a biological drug, an anti-cancer drug, a gene or a fragment thereof, siRNA, a plasmid containing a gene therapy or a gene producing drug or a specific toxin against a disease, a peptide, a protein, a protein fragment or an antisense DNA. Optionally, the drug is an alkaloid, an alkylating agent, an anti-tumor antibiotic, an antimetabolite, a hormone and hormone analog, immunomodulator, photosensitizing agent, antibody, peptide, anti-mitotic agent, or a radiotherapeutic agent.

Some embodiments relate to a plurality of liposomes described above. Optionally, the mean diameter is between 50 nm and 300 nm. Optionally, the mean diameter is between 50 nm and 200 nm. Optionally, the mean diameter is between 50 nm and 150 nm. Optionally, the mean diameter is between 90 nm and 200 nm. Optionally, the zeta potential of a liposome is from −10 mV to −120 mV or from +10 mV to +120 mV. Optionally, the zeta potential of a liposome is from −10 mV to −40 mV or from +10 mV to +40 mV.

Some embodiments relate to a method for treatment comprising administering to a patient in need thereof the plurality of liposomes. Optionally, patient suffers from a disease or pathology of the brain. Optionally, the disease or pathology is selected from the group consisting of: trauma, infections, neurodegeneration, movement disorders, autoimmune CNS indications, Stroke, ADHD, autism, addiction, acoustic neuroma, acquired brain injury, agenesis corpus callosum, Alzheimer's disease, amyotrophic lateral diseases, aneurysm, aphasia, arteriovenous malformation, batten disease, Behçet's disease, blepharospasm, brain tumor, brain cancer, cerebral lupus, cerebral palsy, cervical dystonia, Charcot-Marie-Tooth disorder, Chiari malformation, chronic inflammatory demyelinated polyneuropathy, coma and persistent vegetative state, concussion, Creutzfeldt-Jakob disease, dementia (non-Alzheimer type), Down syndrome, dysautonomia, dyslexia, dyspraxia, dystonia, encephalitis, epilepsy, essential tremor, Friedreich's ataxia, Gaucher disease, Guillain-Barre syndrome, Huntington's disease, hydrocephalus, intracranial hypertension, leukodystrophy, Meniere's disease, meningitis, meningococcal disease, migraine, motor neuron disease, multiple sclerosis, muscular dystrophy, myasthenia gravis, narcolepsy, Parkinson's disease, peripheral neuropathy, Prader-Willi syndrome, progressive supranuclear palsy, restless legs syndrome, Rett syndrome, Shy Drager syndrome, sleep disorders, spasmodic dysphonia, stroke, subarachnoid hemorrhage, Sydenham's chorea, Tay-Sachs disease, Tourette syndrome, transient ischemic attack, transverse myelitis, trigeminal neuralgia, tuberous sclerosis, glioblastoma, neuropathic pain, traumatic brain injury, von-Hippel-Lindau syndrome, a neuroimmune disorder, and a psychiatric disease. Optionally, the disease is brain cancer, selected from the group consisting of: a glioma, a craniopharyngioma, a lymphoma, a hemangioblastomas, a meningiomas, acoustic neuroma/neurinoma, and a pituitary tumor.

In view of the many possible embodiments to which the principles of the disclosed invention may be applied, it should be recognized that the illustrated embodiments are only preferred examples of the invention and should not be taken as limiting the scope of the invention. Rather, the scope of the invention is defined by the following claims. We therefore claim as our invention all that comes within the scope and spirit of these claims.

I claim:

1. A modified peptide having the structure:

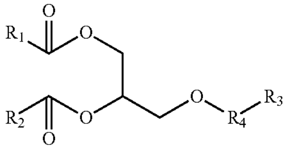

wherein $R_1$ and $R_2$ are each the same or different and are an alkyl chain having between 13 and 19 carbon atoms, $R_3$ is a peptide having a sequence according to SEQ ID NO:1, wherein the methionine residue is oxidized in the form of sulfoxide and wherein $R_4$ is a linker having the structure $R_6$-$R_5$-$R_7$, wherein $R_6$ and $R_7$ are each independently a bond or a carbonyl group; and $R_5$ is selected from the group consisting of: $C_{1-20}$ straight alkyl, $C_{3-20}$ branched alkyl, $C_{3-20}$ cyclic alkyl, and $C_{6-20}$ arylalkyl.

2. The modified peptide according to claim 1 wherein $R_1$ and $R_2$ are a linear alkyl chain having 15 carbon atoms.

3. The modified peptide according to claim 1 wherein the peptide is attached to the linker at the N-terminus of the peptide.

4. The modified peptide according to claim 1 wherein $R_6$ and $R_7$ are each a carbonyl group.

5. The modified peptide according to claim 1 wherein $R_5$ is a $C_{1-6}$ straight alkyl or a $C_{3-6}$ branched alkyl.

6. The modified peptide according to claim 1 wherein $R_5$ is a $C_2$ straight alkyl.

7. A liposome comprising the modified peptide according to claim 1 and further comprising a phospholipid and a cholesterol.

8. The liposome according to claim 7 wherein the phospholipid is 1,2-distearoyl-sn-glycero-3-phosphocholine.

9. The liposome according to claim 7 wherein the molar ratio of phospholipid to cholesterol is between 3:1 and 1:1.

10. The liposome according to claim 7 wherein the modified peptide is present in a molar percentage of 0.05% to 5%, relative to the combined amount of cholesterol and phospholipid.

11. The liposome according to claim 7, and free of 1,2-dioleoyl-sn-glycero-3-phosphocholine (DOPC).

12. The liposome according to claim 7, and free of 1,2-palmitoyl-phosphatidic acid (DPPA).

13. The liposome according to claim 7, further comprising a drug.

14. A plurality of liposomes according to claim 7.

15. The plurality of liposomes according to claim 14 wherein the mean diameter is between 50 nm and 300 nm.

16. The plurality of liposomes according to claim 14 wherein the zeta potential of a liposome is from −10 mV to −120 mV or from +10 mV to +120 mV.

17. The plurality of liposomes according to claim 16 wherein the zeta potential of a liposome is from −10 mV to −40 mV or from +10 mV to +40 mV.

* * * * *